United States Patent [19]

March

[11] 3,958,560

[45] May 25, 1976

[54] NON-INVASIVE AUTOMATIC GLUCOSE SENSOR SYSTEM

[76] Inventor: Wayne Front March, 2517 Rugby Road, Dayton, Ohio 45406

[22] Filed: Nov. 25, 1974

[21] Appl. No.: 526,581

[52] U.S. Cl. .............................. 128/2 A; 128/2 L; 128/2 T; 356/39
[51] Int. Cl.² .......................................... A61B 5/00
[58] Field of Search............. 128/2 A, 2 L, 2 T, 2 E, 128/2.1 E; 351/9; 356/39–41, 51

[56] References Cited

UNITED STATES PATENTS

| | | | |
|---|---|---|---|
| 3,412,729 | 11/1968 | Smith, Jr. ............................. | 128/2 L |
| 3,512,517 | 5/1970 | Kadish et al. ....................... | 128/2 E |
| 3,638,640 | 2/1972 | Shaw.................................... | 128/2 L |
| 3,648,685 | 3/1972 | Hepp et al............................ | 128/2 L |
| 3,769,961 | 11/1973 | Fatt et al............................... | 128/2 T |

OTHER PUBLICATIONS

Nature, Vol. 214, June 3, 1967, pp. 986–988.
California Medicine, June, 1963, Vol. 98, No. 6, pp. 325–327.
Diabetes, Vol. 21, Suppl. 2, 1972, pp. 703–712.

*Primary Examiner*—Kyle L. Howell
*Attorney, Agent, or Firm*—Alter and Weiss

[57] ABSTRACT

A unique glucose sensor to determine the glucose level in patients, for example, for use in treating or diagnosing diabetes. The patient's eye is automatically scanned using a source of radiation at one side of the patient's cornea. A sensor located at the other side of the cornea detects the radiation that passed through the cornea. The level of glucose in the bloodstream of the patient is a function of the amount of radiation detected at the other side of the cornea of the patient. The result is transmitted to a remote receiver that is coupled to a readout device to thereby provide non-invasive glucose determinations.

12 Claims, 3 Drawing Figures

NON-INVASIVE AUTOMATIC GLUCOSE SENSOR SYSTEM

This invention relates to diagnostic and/or curative instruments utilized by modern medicine and more particularly, to non-invasive automatic glucose sensing systems.

At the present, to determine the amount of glucose in the patient's system for thereby determining whether or not the patient has diabetes or has need of insulin, urine or blood specimens are examined. It is well known that the glucose level varies in people. It is especially important to know what the glucose level is in people afflicted with diabetes. In diabetics the level often reaches the point where it is necessary to provide the patient with insulin.

The present method of detecting and treating diabetic patients is for the patient to provide the hospital, doctor or lab technician with the specimens of urine and/or blood which are analyzed. If diabetes is then found, insulin is prescribed. Since the glucose level in each individual is variable, the amount of insulin which the patient takes does not necessarily correlate to the average glucose level. Nonetheless, there is no present method of reliably indicating to the patient that it is necessary for him to take insulin at a certain time or for readily determining the glucose level in the patient's blood. Thus, many patients do not take the necessary insulin when they really need it with the consequent adverse effects. Alternatively, many patients take more insulin than they need and suffer from hypoglycemia.

Thus, the present systems are inadequate because, among other things, they only give instantaneous readings. Further, the blood sample method requires puncturing the skin with a hypodermic device which is inconvenient, time consuming and bothersome. Further, as pointed out, the blood sugar varies widely with variables in the daily routine such as acute illness, diet, physical exercise, etc. This means, that the routine insulin dose may be totally incorrect for a day that is not routine.

Accordingly, an object of the present invention is to provide a convenient way of continuously monitoring the control of glucose level in diabetics.

A further object of the present invenion is to provide sensitive, non-invasive glucose sensors which can diagnose new cases of diabetes.

Yet another object of the present invention is to provide glucose sensing devices that give an automatic readout showing how much glucose is present so that a person with a minimum of training, such as the patient himself, or a simple computer can reliably determine the diabetic control, and therefore, know whether or not to administer insulin.

In accordance with a preferred embodiment of the invention a soft scleral contact lens shaped to fit over the cornea is provided with a built-in energy wave transmitter, such as an infrared source on one side thereof and an infrared detector on the other side. A power source is also mounted in the soft scleral contact lens. The infrared source is aimed to cause the infrared radiation to pass through the cornea and the aqueous humor to the infrared detector. A transmitter is mounted adjacent to the detector and coupled thereto for transmitting a signal that is a function of the infrared level detected. A remote receiver functions to receive the signal transmitted and couple that signal to a readout device which automatically provides a readout determinative of the glucose content in the aqueous humor which is directly proportional to the glucose content of the blood. Switching means may be provided to activate the system.

These and other objects and features of the invention will now be explained with the aid of the accompanying drawings, in which.

Figure 1:
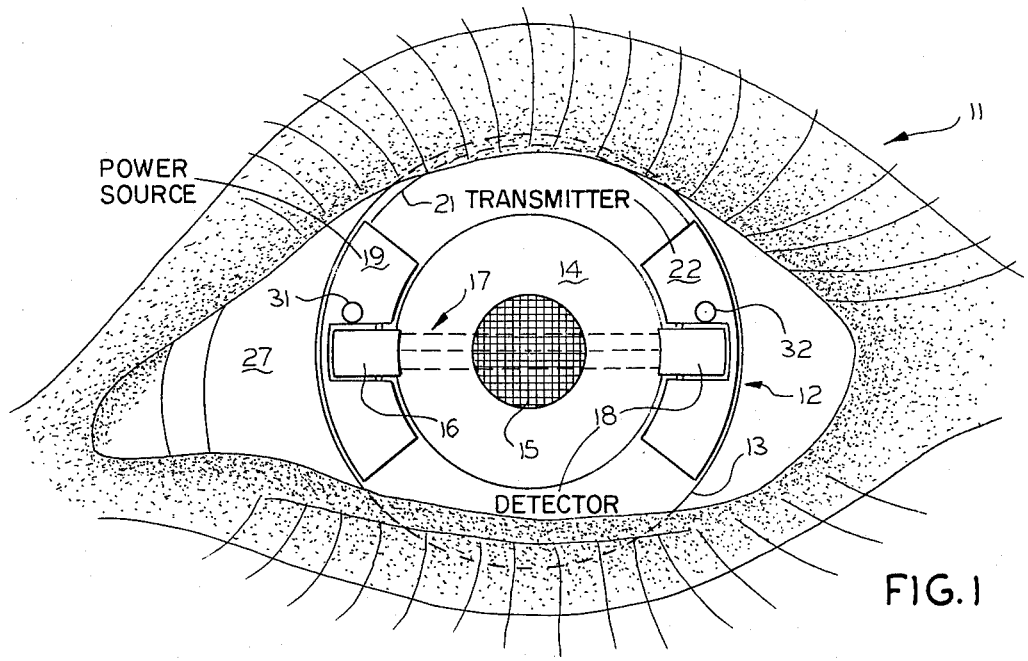
FIG. 1 is a front view of the patient's eyeball having a contact lens thereon which is equipped with the glucose sensor system.

As shown in FIG. 1 the eye, generally shown as 11, is equipped with a non-invasive glucose sensor system, generally shown as 12. The glucose sensor system is mounted into a contact lens 13. The contact lens is preferably a soft scleral contact lens. The lens fits over part of the cornea and part of the sclera 27, covering the iris 14.

Figure 2:
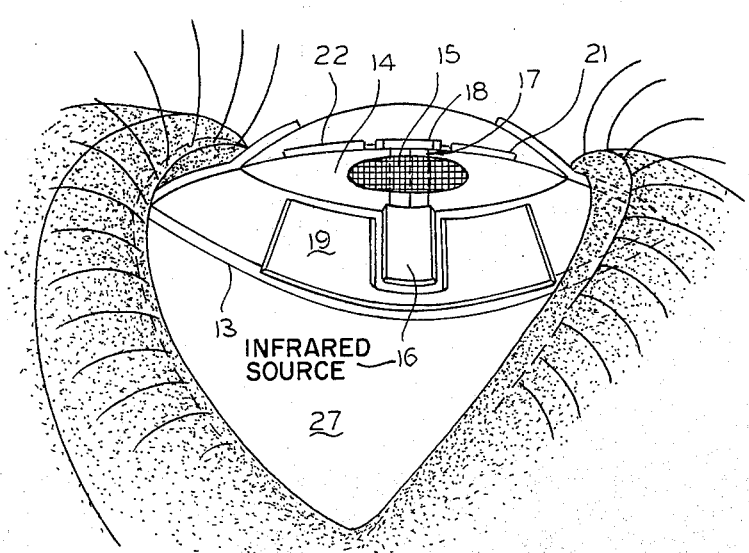
FIG. 2 is a side view of the eyeball of FIG. 1 having the lens thereon with the non-invasive glucose sensor system mounted thereto.

As can be seen particularly, in FIG. 2, the cornea covering the iris 14 and the pupil 15 resembles a mound in that it has a different radius of curvature and, therefore, rises above the level of the rest of the eyeball. The non-invasive glucose sensor system is shown mounted at the periphery of the iris. Radiation source means are provided. For example, an infrared source 16 is shown mounted in the contact lens at one side of the iris. It emits an infrared radiation shown at 17, which is received by the infrared radiation detector 18. The amount of radiation received by the infrared radiation detector 18 is a function of the amount of glucose in the patient's blood.

Also, shown is a power source 19 mounted in the contact lens which may be any well known small nickel cadmium battery, for example, coupled to the infrared source 16 to provide it with the necessary power. The battery is shown coupled to the detector through conductor 21.

One preferrable source of infrared radiation is a zirconium filament light bulb emitting a ray having a wave length of 0.975 microns. The detector used may be a thermistor bolometer. It should be understood that other radiation emitting and detecting devices are within the scope of this invention. For example, visible light may be similarly directed and detected by an interferometer which will measure the change in refractive index produced by the glucose content in the aqueous humor.

The detector 18 is shown at the other side of the iris, mounted in the soft scleral lens. The detected infrared radiation is a function of the sugar content because the hydroxyl in glucose affects the infrared radiation, thereby changing the amount of infrared detected by detector 18.

Means are provided for transmitting the detector output. More particularly, transmitter 22 sends the detected signal that is received at receiver 23. The signal from receiver is amplified at amplifier 24 which is connected to a readout device 26. The readout device is preferably a direct digital readout device. This receiver and readout device are only shown in block diagram form, since many different modes of receiver and readout can be used.

Most cases of diabetes cannot be cured, but almost all may be controlled by injections of insulin and careful attention to diet. The diabetic learns to test his urine for sugar and to give himself injections of insulin to augment the failure of the pancreas to produce enough of that hormone.

Figure 3:
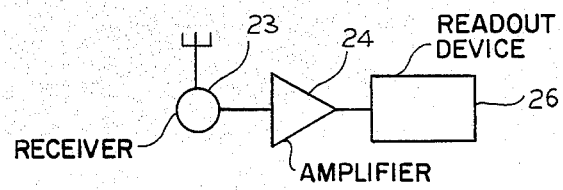
FIG. 3 is a block diagram showing of a receiving system providing a readout of the glucose content as determined by the non-invasive sensor system.

In practice the patient slips the soft scleral contact lens over his eye and automatically, with no appreciable impairment to his vision, the glucose system is in position to transmit a signal that is a function of the glucose content in blood. He may either carry the receiving and readout device, as shown in FIG. 3, or may utilize it in his home. The patient is able to determine from the readout device whether or not he needs to inject more insulin or alter his diet.

A switching arrangement is indicated at 31 and 32. The switches 31 and 32 in series between the power source and the source 16 and the detector 18 are micro switch varieties which are operated by pressure applied, such as through the closure of the patient's eyelids to start and stop the system. Alternatively, the switching devices 31 and 32 could operate on a time basis or on a start signal basis. For example, the glucose sensor can be programmed to readout either on a time basis — once every hour — or else upon receiving a signal from a start transmitter (not shown) carried by the patient, and then run for a specific time period.

While the principles of the invention have been described above in connection with specific apparatus and applications, it is to be understood that this description is made only by way of example, and not as a limitation on the scope of the invention. For example, since the body in general, and in particular, the iris at 98.6° F is, in itself, a source of infrared radiation at low amplitude, it may be possible, after further improvement in the sensitivity of the detector, to eliminate the artificial infrared source entirely. Again, as better detectors are developed, it may be also possible to employ other types of radiation than infrared.

I claim:

1. A non-invasive glucose sensor system for determining the sugar content in the user's blood,
    said system comprising radiation source means for emitting radiation of certain wave lengths,
    said certain wave lengths being altered by sugar derivatives,
    radiation detecting means for detecting said certain wave lengths,
    power source means for providing power to said radiation source means and said radiation detecting means,
    mounting means for mounting said radiation emitting means and radiation detecting means spaced apart from each other, but in line with each other, so that the radiation detecting means receives the certain wave lengths of the radiation source means, the distance said radiation source means and said radiation detecting means are spaced apart being at least equal to the diameter of the cornea of the human eye,
    said mounting means being adapted to be fitted contiguous to a user's eye with said radiation source means and radiation detecting means at opposite sides of the cornea of the human eye so that said radiation of said certain wave lengths passes through the cornea of the user's eye in going to the radiation detecting means, and
    said radiation detecting means comprising indicator means for indicating the sugar content of the user's blood as a function of the detected radiation.

2. The non-invasive glucose sensor system of claim 1 wherein said means for mounting said radiation emitting means and said radiation detecting means comprises contact lens means.

3. The non-invasive glucose sensor system of claim 2 wherein said contact lens means is a soft scleral contact lens.

4. The non-invasive glucose sensor system of claim 2 wherein said radiation emitting means is mounted in the contact lens substantially at that portion of the contact lens that is at the periphery of the user's iris, and wherein said detector means is mounted opposite to said emitter means on the contact lens at the periphery of the user's iris, when the sensor is in use.

5. The non-invasive glucose sensor system of claim 1 wherein said radiation emitting means comprises means for emitting infrared radiation, and wherein said detecting means comprises means for detecting infrared radiation.

6. The non-invasive glucose sensor system of claim 1 wherein means are provided for transmitting a signal that is a function of the detected radiation obtained from said radiation detector means and receiving means for receiving said transmitted signal to provide an indication of the glucose content of the user's blood.

7. The non-invasive glucose sensor system of claim 6 wherein said receiving means includes digital readout means for digitally providing a readout determinative of the glucose content of the user's blood.

8. The non-invasive glucose sensor system of claim 7 wherein switching means are provided for selectively actuating said system.

9. The non-invasive glucose sensor system of claim 8 wherein said switching means comprises pressure sensitive switches which are actuated by the user through his eyelids.

10. A method of obtaining a direct reading of sugar content of a person non-invasively and automaticaly, said method comprising the steps of: transmitting radiation rays through the cornea of the patient's eye; detecting radiation rays which have passed through the cornea of the patient's eye; translating the detected radiation rays to obtain a readout indicative of the sugar content in the patient's blood.

11. The method of claim 10 including the steps of transmitting a signal that is a function of the detected radiation, receiving the detected signal and translating the received, detected signal into a digital readout indicative of the sugar content of the person's blood.

12. The method of claim 11 including the step of mounting said transmitting means and said detecting means, as well as transmitter means onto a contact lens and placing the contact lens in the patient's eye, and then selectively actuating the radiation emitting means, the radiation detecting means and the transmitting means.

* * * * *